United States Patent [19]

DuPriest et al.

[11] Patent Number: 5,151,544
[45] Date of Patent: Sep. 29, 1992

[54] INTERMEDIATES IN THE PREPARATION OF CHIRAL SPIROFLUORENEHYDANTOINS

[75] Inventors: Mark T. DuPriest; Raymond E. Conrow; Daniel Kuzmich, all of Fort Worth, Tex.

[73] Assignee: Alcon Laboratories, Inc., Fort Worth, Tex.

[21] Appl. No.: 530,766

[22] Filed: May 25, 1990

[51] Int. Cl.⁵ .................. C07C 321/00; C07C 229/00
[52] U.S. Cl. ........................ 560/10; 560/34; 560/45; 560/47; 560/48
[58] Field of Search ........ 560/34, 45, 10, 47, 560/48

[56] References Cited

U.S. PATENT DOCUMENTS

| | | | |
|---|---|---|---|
| 4,117,230 | 9/1978 | Sarges | 548/309 |
| 4,286,098 | 8/1981 | Sarges | 548/309 |
| 4,348,526 | 9/1982 | Sarges | 548/309 |
| 4,419,521 | 12/1983 | Sarges | 549/404 |
| 4,436,745 | 3/1984 | York, Jr. | 424/273 |
| 4,438,272 | 3/1984 | York, Jr. | 548/308 |
| 4,540,700 | 9/1985 | York, Jr. | 514/278 |
| 4,716,113 | 12/1987 | Urban | 435/125 |
| 4,864,028 | 9/1989 | York, Jr. | 546/15 |
| 4,952,694 | 8/1990 | Brackeen et al. | 546/15 |

OTHER PUBLICATIONS

Sarges, et al., "Synthesis of Optically Active Spirohydantoins by Asymmetric Induction. Hydantoin Formation from Amino Nitriles and Chlorosulfonyl Isocyanate", *J. Org. Chem.*:47(21) 4081–4085 (1982).

Okamoto, et al., "Controlled Chiral Recognition of Cellulos Triphenylcarbamate Derivatives Supported on Silica Gel", *J. Chromatography*:363, 173–186(1986).

*Primary Examiner*—Mary C. Lee
*Assistant Examiner*—Robert C. Whittenbaugh
*Attorney, Agent, or Firm*—Gregg C. Brown; Barry L. Copeland

[57] ABSTRACT

Disclosed is a process for the synthesis of enantiomerically pure R and S isomers of 2,7-difluoro-4-methoxyspiro[9H-fluorene-9,4-imidazolidene]-2',5'-dione from 2,7-difluoro-4-methoxyfluorenone. Intermediate amino acid esters and urea esters and their preparation are also described.

8 Claims, No Drawings

INTERMEDIATES IN THE PREPARATION OF CHIRAL SPIROFLUORENEHYDANTOINS

BACKGROUND OF THE INVENTION

1. Field of the Invention

This invention relates to a novel process for the synthesis of certain chiral spirofluorenehydantoins, which may be used in the treatment of complications arising from diabetes mellitus. The invention also relates to novel intermediate compounds, which are integral to the claimed process.

2. Description of Related Art

Racemic and the R and S enantiomers of certain chiral spirofluorenehydantoins have previously been reported to be aldose reductase inhibitors and thus of value in controlling complications arising from diabetes mellitus (e.g., diabetic cataracts and neuropathy). Reference is made to commonly assigned U.S. Pat. No. 4,864,028 (York) for further background in this regard. The entire contents U.S. Pat. No. 4,864,028 relating to the utility, structure and synthesis of such chiral spirofluorenehydantoins are hereby incorporated in the present specification by reference.

Methods of obtaining enantiomerically pure forms of chiral hydantoins have been described previously. Prior methods have involved resolution using the resolving agent brucine, or asymmetric synthesis using a method similar to a procedure described in Sarges, et al., *J. Org. Chem.*, 47:4081 (1982). The present inventors have found that the R and S enantiomers of certain substituted spirofluorenehydantoins, such as 2,7- difluoro-4-methoxyspiro[9H-fluorene-9,4′imidazolidine]-2′5′-dione, cannot be obtained via such prior methods. There is, therefore, a need for a method of synthesizing these enantiomers. The present invention is directed to fulfilling this need. More particularly, the method of this invention provides for the synthesis of the pure R and S enantiomers of the subject compounds.

SUMMARY OF THE INVENTION

The present invention provides a method for the synthesis of the R and S enantiomers of chiral spirofluorenehydantoins of the structure:

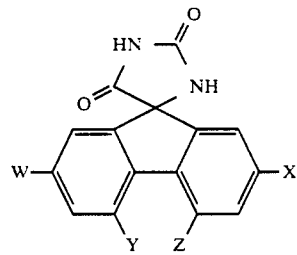

wherein:
W and X are each, independently of the other, selected from the group consisting of hydrogen, chloro and fluoro;
one of Y and Z is selected from the group consisting of hydrogen, chloro, fluoro, methyl, methoxyl and methylthio and the other is selected from the group consisting of hydrogen, chloro and fluoro;
with the proviso that W, X, Y and Z are selected such that the substituted pattern does not result in a symmetrical molecule;

and pharmaceutically acceptable salts thereof. The compounds are prepared from the corresponding fluorenones.

The reaction scheme may be summarized as involving the following five steps:

Step 1 - Condensation wherein R = a $C_2$-$C_6$ carboxylic ester or aryl

Step 2 - Deprotonation/Acylation/Hydrolysis

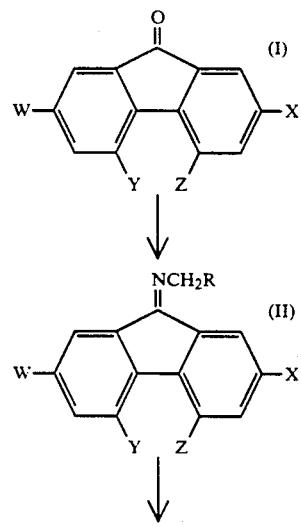

-continued

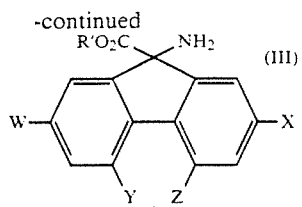

wherein R' = $C_1-C_5$ alkyl

Step 3 - Chromatographic or chemical resolution

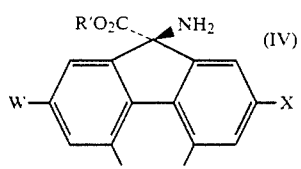
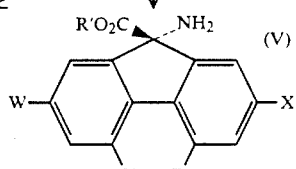

Step 4 - Urea Formation

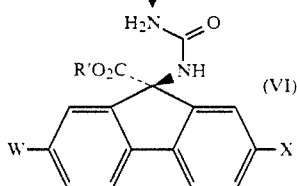
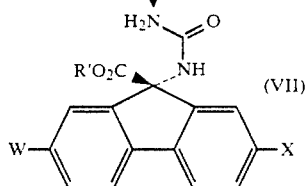

Step 5 - Cyclization

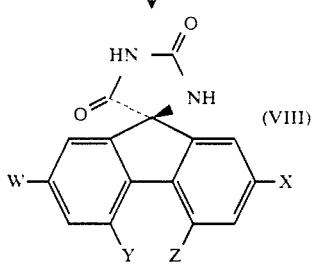
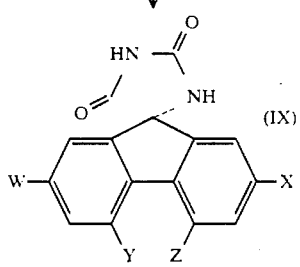

The process comprises condensing the fluorenone (I) with an amine, preferably benzylamine, to form the imine of structure (II), which is then deprotonated and acylated at C-9 with a lower alkyl chloroformate. In situ hydrolysis of the resulting imine provides the amino acid ester of structure (III), which is then resolved to provide the R and S amino acid esters (IV) and (V), each of which is then reacted with a source of cyanate to form the R and S urea esters (VI) and (VII), which are each then cyclized to the spirofluorenehydantoins (VIII) and (IX). The invention also relates to the novel intermediate compounds of structures (IV), (V) (VI) and (VII).

DETAILED DESCRIPTION OF THE INVENTION

In words relative to the above schematic representations, the five-step synthesis of the R and S enantiomers of the subject compounds is described in greater detail below.

The starting fluorenones (I) may be synthesized according to known procedures, for example the procedures described in U.S. Pat. No. 4,864,028, or procedures otherwise known to those skilled in the art. The initial step of the synthesis, conversion of (I) to the imine (II) by reaction with a glycine ester or a substituted or unsubstituted benzylamine, preferably benzylamine, may be carried out in an inert, anhydrous solvent, such as an aromatic hydrocarbon (e.g. benzene, toluene), an ether (e.g., tetrahydrofuran, dioxane, diethyl ether, 1,2-dimethoxyethane), or a halogenated solvent such as methylene chloride. The reaction is preferably carried out under conditions wherein the water is removed from the reaction mixture either azeotropically (e.g., with benzene or toluene) or by the addition of a dehydrating agent such as titanium tetrachloride. Higher yields of the desired imine are obtained using titanium tetrachloride as the dehydrating agent. The temperature for the reaction can be in the range of −10° C. to 15° C. Above 15° C. the yield of the desired imine (II) is significantly reduced. The preferred temperature is in the range of 0° C. to 15° C. The molar ratio of ketone, amine and titanium tetrachloride is not critical. It can range from theoretical (1:1:0.5) to 1:4:0.75, with an added base such as a tertiary amine (e.g., triethylamine) to neutralize the hydrogen chloride produced as a by-product in the reaction or during isolation (e.g., four moles of base per mole of titanium tetrachloride). If desired, an excess of the amine reactant itself can be used as the base for neutralization of the hydrogen chloride.

The second step of the five-step sequence comprises deprotonation of (II) at the benzylic position to form a delocalized anion which is then acylated and hydrolyzed. The deprotonation is usually carried out at a temperature of −70° C. to 45° C. using a base such as butyllithium, lithium diisopropylamide, or sodium hydride in an inert, anhydrous solvent, such as an aromatic hydrocarbon (e.g., benzene, toluene) or an ether (e.g. tetrahydrofuran, dioxane, diethyl ether, 1,2-dimethoxyethane) optionally containing a polar cosolvent (e.g., N,N,N',N'-tetramethylethylenediamine (TMEDA) or hexamethylphosphoramide (HMPA)). The preferred combination is sodium hydride in tetrahydrofuran at a temperature of 30° C. to 45° C. Under these conditions deprotonation is judged to be complete when the evolution of hydrogen gas ceases. Generally, a 10% to 30% excess of the base is employed to ensure complete deprotonation. The reaction mixture is then cooled to 0° C. to 15° C. and a two to four-fold molar excess of an alkyl chloroflormate is added. Methyl chloroformate is preferred, though any $C_1$ to $C_5$ alkyl chloroformate can be used. The reaction mixture is then stirred for a period of 30 minutes to 2 hours while warming to room temperature. After this period of time, the mixture is again cooled to 0° C. to 15° C. and aqueous hydrochloric acid is added to hydrolyze the imine intermediate to yield the desired compound (III). In principle, any strong mineral acid (e.g. sulfuric acid or nitric acid) would be sufficient. The product is conveniently isolated by extraction into aqueous acid followed by neutralization and filtration.

The third step of the sequence is the resolution of (III) to provide the R(+) and S(−) enantiomers, (IV) and (V) respectively. This can be accomplished by a number of methods known to those skilled in the art, including diasteriomeric salt formation with an acid such as L-tartaric acid, conversion to diasteriomeric amides followed by chemical or chromatographic separation and hydrolysis, or chiral chromatography. The preferred method is by use of a Chiralcel OF column such as that described in Okamoto, et al., *J. Chromatogr*, 363:173 (1986), and a mixed solvent system consisting of hexane and isopropanol, preferably in the ratio of 2 to 1.

The fourth and fifth steps of the synthesis are carried out on enantiomer (IV) or (V) depending on which enantiomer of the spirofluorenehydantoin is desired. Proceeding with (IV) provides the R(+) enantiomer (VIII), while the S(−) enantiomer (IX) is obtained from (V).

In either case, in the fourth step of the synthesis, the R(+) or S(−) amino acid ester, (IV) or (V) respectively, is reacted with cyanate (sodium or potassium salts are preferred) in a suitable organic acid, preferably acetic acid, at 45° C. to 100° C. for 15 minutes to 1 hour. At a temperature of 60²⁰ C., a reaction time of 30 minutes should be sufficient. The product is conveniently isolated by diluting the reaction mixture with ice water and collecting the product by filtration. At least a 1:1 ratio of the cyanate to the amino acid ester is required for high yields; a two to three-fold excess of cyanate is not detrimental.

In the fifth and final step of the synthesis, a mixture of the R(+) or S(−) urea ester (VI or VII), and an inorganic base such as potassium carbonate is stirred in a solvent such as methanol or ethanol at a temperature in the range of 0° C. to 45° C. Generally, the molar ratio of the base to urea ester is in excess of 1:1, ranging from 1:1 to 3:1. Cyclization occurs at such a rate that the reaction is complete after 30 minutes at room temperature in methanol. The progress of the reaction can be conveniently monitored using thin layer chromatography on silica gel plates with a methanol/methylene chloride solvent mixture. The R(+) or S(−) spirofluorenehydantoin product ((VII) or (VIII) respectively) is easily isolated by solvent evaporation and addition of dilute mineral acid to the residue, at which point the product can be collected by filtration.

The synthesis of the present invention is further illustrated by the following examples, wherein a specific embodiment of the invention is described in detail. However, it should be understood that the invention is not limited to the specific details of these examples.

EXAMPLE 1

N-(2,7-Difluoro-4-methoxyfluoren-9-ylidene)benzylamine (II)

Titanium tetrachloride (0.127 mol, 127 mL of a 1.0 M methylene chloride solution) was added dropwise over a 15 minute to a mechanically stirred suspension of 2,7-difluoro-4-methoxyfluorenone (I) (50.0 g, 0.203 mol) and benzylamide (81 g, 0.76 mol) in methylene chloride (1 L) under nitrogen, keeping the temperature below 15° C. The mixture was stirred for 30 min while warming to 24° C., and then filtered through a pad of Florisil, washing with diethyl ether (4 L). The filtrate was concentrated to 500 mL and diluted with hexane (500 mL). The precipitated yellow imine was collected by filtration and combined with second and third crops obtained by concentration of the mother liquor to provide a total of 64 g (94%) of (II) as mixture of geometric isomers: IR (KBr) 1648, 1617, 1603, 1592, 1469, 1452, 1321, 1294 $cm^{-1}$; $^1$H NMR ($CDCl_3$, 200 $MH_z$)δ7.95-6.40 (m, 10 H), 5.26 and 5.27 (singlets, total 2 H), 3.94 and 3.96 (singlets, total 6 H).

EXAMPLE 2

(3S)-9-Amino-2,7-difluoro-4-methoxyfluorene-9-carboxylic acid methyl ester (III)

The imine (II) (30 g, 90 mmol) was added in portions over a 5 minute period to a mechanically stirred suspension of hexane washed sodium hydride (0.11 mol, 4.5 g of a 60% oil dispersion) in anhydrous tetrahydrofuran (300 mL) (distilled from lithium aluminum hydride) at 45° C. under nitrogen. After 40 minutes, the mixture was cooled to 10° C. and a solution of methyl chloroformate (0.27 mol, 21 mL) in tetrahydrofuran (40 mL) was added, keeping the temperature below 12° C. The reaction mixture was stirred for 1 hour while warming to 24° C., then cooled to 10° C., quenched with 100 mL of 1 M aqueous hydrochloric acid, and stirred (to 24° C.) for 1 hour. The mixture was diluted with 500 mL of 1:1 ether/hexane and the amine hydrochloride was extracted with 1 M aqueous hydrochloric acid. The aqueous solution was neutralized using sodium bicarbonate and the precipitated product was collected by filtration. The solid was dissolved in ethyl acetate (800 mL) and the solution was dried over $MgSO_4$, decolorized with Norit A, filtered through Celite, and concentrated. The residue was triturated with ether and then recrystallized from ethyl acetate/hexane to provide 20.7 g (76%) of III: mp 153°–155° C. The mother liquor was concentrated and the residue chromatographed on silica gel using a gradient of pure methylene chloride to 5% methanol in methylene chloride to give an additional 1.6 g (6%) of material. IR (KBr) 3389, 3317, 1733, 1598 cm$^{-1}$; $^1$H NMR (CDCl$_3$,200 MHz)δ7.90 (dd, 1 H,J=5.2, 8.5 Hz), 7.18 (dd, 1H,J=2.4, 8.3 Hz), 7.04 (ddd, 1 H, J=2.5, 8.4, 9.1 Hz), 6.84 (dd, 1 H, J=2.1, 7.8 Hz), 6.66 (dd, 1 H, J=2.0, 11.1 Hz), 3.97 (s, 3 H), 3.60 (s, 3 H), 2.25 (bs, 2 H); MS m/z 305 (M+), 246 (base peak).

Analysis for C$_{16}$H$_{13}$F$_2$NO$_3$. Calcd: C,62.95; H, 4.29; N, 4.29. Found: C, 62.84; H, 4.10; N, 4.53.

EXAMPLE 3

Chromatographic resolution of (III)

The chromatographic resolution of III was accomplished on a preparative scale using a Chiralcel OF column and 2:1 hexane/isopropanol. Twenty-seven grams of each enantiomer were provided from 100 grams of the racemic material. The first eluted isomer (IV) had a rotation in methanol of +1.14°, while the second eluted isomer (V) had a rotation of −1.26°.

EXAMPLE 4

R-(+)-2,7-Difluoro-4-methoxy-9-ureidofluorene-9-carboxylic acid methyl ester (VI)

A mixture of R-(+)-9-amino-2,7-difluorofluorene-9-carboxylic acid methyl ester (IV) (10.0 g, 32.8 mmol) and sodium cyanate (2 eq, 4.4 g) in acetic acid (100 mL) was heated at 60° C. for 30 minutes. The mixture was then diluted with ice-water (800 mL) and the solid was collected by filtration, washing with water, and air dried to provide 11.4 g (100%) of VI: mp 252°–254° C.; IR (KBr) 3449, 3381, 1728, 1716, 1687 cm$^{-1}$; $^1$H NMR (DMSO-d$_6$, 200 MHz) δ7.86 (dd, 1 H, J=5.3, 8.5 Hz), 7.50 (dd, 1 H, J=2.6, 9.0 Hz), 7.26 (m, 2 H), 7.12 (dd, 1 H, J=2.2, 8.5 Hz), 7.04 (dd, 1 H, J=2.2, 11.8 Hz), 5.75 (s, 2 H), 3.98 (s, 3 H), 3.56 (s, 3 H); MS m/z 348 (M+), 246 (base peak); [α]$_D^{25}$= +5.17°(c=0.5, methanol).

Analysis for C$_{17}$H$_{14}$F$_2$N$_2$O$_4$. Calcd: C, 58.62; H, 4.05; N, 8.04. Found: C, 58.55; H, 3.66; N,7.94.

EXAMPLE 5

S-(−)-2,7-Difluoro-4-methoxy-9-ureidofluorene-9-carboxylic acid methyl ester (VII)

A mixture of S-(−)-9-amino-2,7-difluorofluorene-9-carboxylic acid methyl ester (IV) (14.0 g, 45.9 mmol) and sodium cyanate (2.2 eq, 6.2 g) in acetic acid (140 mL) was heated at 60° C. for 30 minutes. The mixture was then poured into water (1 L) and the solid was collected by filtration, washing with water, and air dried. This run plus a second run on 10 g of IV provided a total yield of 27 g (99%) of VII: mp 252°–256° C.; IR (KBr) 3450, 3381, 1728, 1716, 1687 cm$^{-1}$; $^1$H NMR (DMSO-d$_6$, 200 MH2)δ7.85 (dd, 1 H, J=5.3, 8.5 Hz), 7.49 (dd, 1 H, J=2.5, 9.0 Hz), 7.25 (m, 2 H), 7.11 (dd, 1 H, J=2.2, 8.5 Hz), 7.03 (dd, 1 H, J=2.2, 11.6 Hz), 5.75 (s, 2 H), 3.96 (s, 3 H), 3.55 (s, 3 H); MS m/z 348 (M+), 246 (base peak); [α]$_D^{25}$= −7.96° (c=0.5, methanol).

Analysis for C$_{17}$H$_{14}$F$_2$N$_2$O$_4$. Calcd: C, 58.62; H, 4.05; N, 8.04. Found: C, 58.60; H, 4.04; N, 7.88.

EXAMPLE 6

R-(+)-2,7-Difluoro-4-methoxyspiro[9H-fluorene-9,4′-imidazolidine]-2′,5′-dione (VIII)

A suspension of R-(+)-2,7-difluoro-4-methoxy-9-ureidofluorene-9-carboxylic acid methyl ester (VI) (9.6 g, 27.6 mmol) and potassium carbonate (9.6 g) in methanol (200 mL) was stirred at room temperature for 30 minutes. The methanol was then evaporated and the residue was acidified with aqueous 1 M hydrochloric acid and filtered, washing with water. The solid was dissolved in warm ethyl acetate, dried over MgSO$_4$, treated with Norit A, filtered through celite, and concentrated. The material so obtained, when combined with that from 3 similar runs, was first leached with acetonitrile, filtered at 10° C., and then recrystallized from acetonitrile/tetrahydrofuran to provide first and second crops of 18.1 and 2.2 g, respectively. The yield for the conversion of 28 g of VI to VIII in four runs was 80%. mp 300°–304° C.; IR (KBr) 3430, 2735, 1787, 1731 cm$^{-1}$; $^1$H NMR (DMSO-d$_6$, 200 MHz)δ11.28 (s, 1 H, exchangeable), 8.64 (s, 1 H, exchangeable), 7.86 (dd, 1 H, J=5.3, 8.4 Hz), 7.43 (dd, 1 H, J=2.4, 8.6 Hz), 7.28 (ddd, 1 H, J=2.5, 8.1, 8.1 Hz), 7.05 (m, 2 H), 3.98 (s, 3 H); MS m/z 316 (M+),245 (base peak); [α]$_D^{25}$=14.2° (c=1, methanol).

Analysis for C$_{16}$H$_{10}$F$_2$N$_2$O$_3$. Calcd: C, 60.76; H, 3.19; N, 8.86. Found: C, 60.98; H, 3.12; N, 8.87.

EXAMPLE 7

S-(−)-2,7-Difluoro-4-methoxyspiro[9H-fluorene-9,4′-imidazolidine]-2′,5′-dione (IX)

A suspension of S-(−)-2,7-difluoro-4-methoxy-9-ureidofluorene-9-carboxylic acid methyl ester (VII) (27.0 g, 77.6 mmol) and potassium carbonate (27 g) in methanol (500 mL) was stirred at room temperature for 30 minutes. The methanol was then evaporated and the residue was acidified with aqueous 1 M hydrochloric acid and filtered, washing with water. After air drying overnight, the solid was dissolved in refluxing ethyl acetate (800 mL), dried over MgSO$_4$, treated with Norit A, and filtered through celite. Solvent removal left 24.3 g of crude material which was leached with acetonitrile and filtered at 0° C. The acetonitrile filtrate was evaporated and the residue (2.5 g) was chromatographed on silica gel using first 25% and then 50% ethyl acetate in hexane to provide additional material which was combined with that obtained by filtration at 0° C. Recrystallization from acetonitrile/tetrahydrofuran provided first and second crops of 15.5 and 5 g, respectively, for a total yield of (IX) of 20.5 g (84%). mp 300°–304° C.; IR (KBr) 3430, 2735, 1787, 1731, 1602, 1316 cm$^{-1}$; $^1$H NMR (DMSO-d$_6$, 200 MHz)δ11.29 (s, 1 H, exchangeable), 8.64 (s, 1 H exchangeable), 7.87 (dd, 1 H, J=5.2, 8.5 Hz), 7.43 (dd, 1 H, J=2.4, 8.5 Hz), 7.28 (bddd, 1 H, J=2.5, 8.1, 8.1 Hz), 7.05 (m, 2 H), 3.98 (s, 3 H); MS m/z 316 (M+), 245 (base peak); [α]$^{25}$= −13.80° (c=1, methanol). D Analysis for C$_{16}$H$_{10}$F$_2$N$_2$O$_3$. Calcd: C, 60.76; H, 3.19; N, 8.86. Found: C, 60.92; H, 3.09; N. 8.85.

We claim:

1. A compound of the formula:

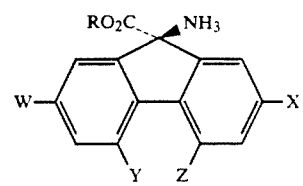

wherein:
R=C$_1$–C$_5$ alkyl;

W and X are each, independently of the other, selected from the group consisting of hydrogen, chloro and fluoro;

one of Y and Z is selected from the group consisting of hydrogen, chloro, fluoro, methyl, methoxyl and methylthio and the other is selected from the group consisting of hydrogen, chloro and fluoro;

with the proviso that the W, X, Y and Z are selected such that the resulting compounds are asymmetrical;

or a pharmaceutically acceptable salt thereof.

2. A compound of the formula:

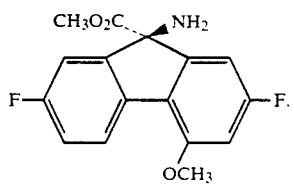

3. A compound of the formula

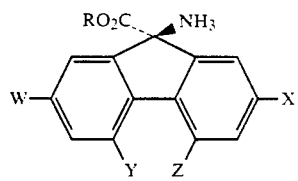

wherein:
$R = C_1-C_5$ alkyl;

W and X are each, independently of the other, selected from the group consisting of hydrogen, chloro and fluoro;

one of Y and Z is selected from the group consisting of hydrogen, chloro, fluoro, methyl, methoxyl and methylthio and the other is selected from the group consisting of hydrogen, chloro and fluoro;

with the proviso that the W, X, Y and Z are selected such that the resulting compounds are asymmetrical;

or a pharmaceutically acceptable salt thereof.

4. A compound of the formula

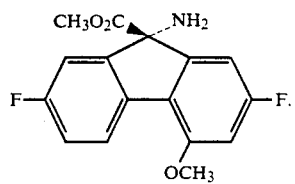

5. A compound of the formula

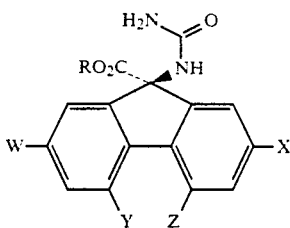

wherein
$R = C_1-C_5$ alkyl;

W and X are each, independently of the other, selected from the group consisting of hydrogen, chloro and fluoro;

one of Y and Z is selected from the group consisting of hydrogen, chloro, fluoro, methyl, methoxyl and methylthio and the other is selected from the group consisting of hydrogen, chloro and fluoro;

with the proviso that the W, X, Y and Z are selected such that the resulting compounds are asymmetrical;

or a pharmaceutically acceptable salt thereof.

6. A compound of the formula:

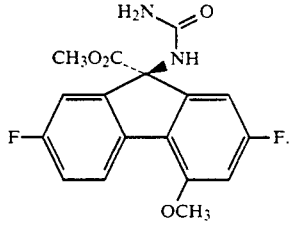

7. A compound of the formula:

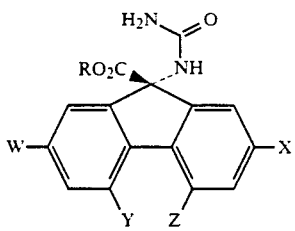

wherein
$R = C_1-C_5$ alkyl;

W and X are each, independently of the other, selected from the group consisting of hydrogen, chloro and fluoro;

one of Y and Z is selected from the group consisting of hydrogen, chloro, fluoro, methyl, methoxyl and methylthio and the other is selected from the group consisting of hydrogen, chloro and fluoro;

with the proviso that the W, X, Y and Z are selected such that the resulting compounds are asymmetrical;

or a pharmaceutically acceptable salt thereof.

8. A compound of the formula:

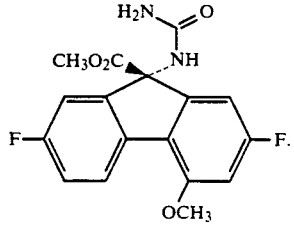

* * * * *

UNITED STATES PATENT AND TRADEMARK OFFICE
CERTIFICATE OF CORRECTION

PATENT NO. : 5,151,544
DATED      : September 29, 1992
INVENTOR(S) : DuPriest, et al.

It is certified that error appears in the above-identified patent and that said Letters Patent is hereby corrected as shown below:

Column 4, formula (IX), that portion of the formula reading

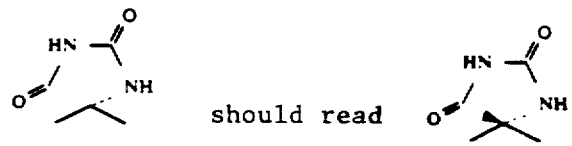

Column 5, line 60, "6020C." should read --60°C.--.
Column 6, line 44, that portion of the compound name reading "(35)-9-Amino" should read --(±)-9-Amino--.
Column 8, that portion of the formula of claim 1 reading

Column 9, that portion of the formula of claim 3 reading

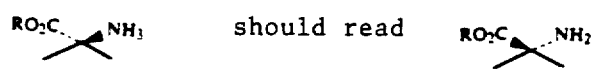

Signed and Sealed this

Second Day of November, 1993

Attest:

BRUCE LEHMAN

Attesting Officer    Commissioner of Patents and Trademarks